United States Patent [19]

Kitamori et al.

[11] 4,372,968

[45] Feb. 8, 1983

[54] GRANULES OF SODIUM ASCORBATE AND THE PRODUCTION THEREOF

[75] Inventors: Nobuyuki Kitamori, Suita; Keizi Hemmi, Osaka; Masaya Maeno, Suita, all of Japan

[73] Assignee: Takeda Chemical Industries, Ltd., Osaka, Japan

[21] Appl. No.: 201,965

[22] Filed: Oct. 29, 1980

[51] Int. Cl.$^3$ ............................................. A61K 31/365
[52] U.S. Cl. ..................................................... 424/280
[58] Field of Search ......................................... 424/280

[56] References Cited

U.S. PATENT DOCUMENTS 3,493,659  2/1970  Magid ................................. 424/280
4,036,948  7/1977  Kitamori et al. ............... 424/280 X

*Primary Examiner*—Douglas W. Robinson
*Attorney, Agent, or Firm*—Wenderoth, Lind & Ponack

[57] ABSTRACT

Granules of higher potency of sodium L-ascorbate obtainable by spray-coating sodium L-ascorbate powder in a fluidized-bed granulator with a binder are excellent in terms of color stability and flowability.

Tablets obtainable by compressing the granules have a satisfactory mechanical strength.

22 Claims, No Drawings

GRANULES OF SODIUM ASCORBATE AND THE PRODUCTION THEREOF

The present invention relates to sodium L-ascorbate granules, and to a process for producing the same.

Sodium L-ascorbate is administered in the form of tablets. Yet, in view of its large dose, tablets with increased content of sodium L-ascorbate are required.

Since sodium L-ascorbate, in the powder form, cannot be directly compressed into tablets, manufacture of tablets containing sodium L-ascorbate is carried out by kneading sodium L-ascorbate powder, together with an excipient as the case may be, with a solution containing a binder to produce granules, followed by compressing them into tablets. However, the sodium L-ascorbate tablets obtained in this manner contain large quantities of the excipient and binder, resulting in decreased amount of sodium L-ascorbate contained in the tablet.

U.S. Pat. No. 3,493,659, with a specific view to the manufacture of granules and tablets with increased content of sodium ascorbate, discloses a process which comprises granulating by the kneading method a mixture consisting of about 90 to 97% of sodium ascorbate and about 3 to 10% of pre-gelatinized starch, and compressing directly it into tablets. However, the kneading process requires the use of large quantities of water, and the process, therefore, suffers from the drawbacks that the resulting granules are colored and that the tablets produced with the use of such granules are also colored.

The present inventors, after extensive research conducted with a view to obtaining less colored sodium L-ascorbate granules and less colored tablets with the use of such granules, found that, by means of a fluidized-bed granulator capable of controlling the water content, sodium L-ascorbate powder while allowing it to fluidize in the fluidized-bed granulator is sprayed with a solution containing a binder, thereby ensuring granulation with extremely depressed color change.

In the next place, it is likely that an increased content of sodium L-ascorbate in the granule would not lead to satisfactory mechanical strength of the tablet obtained by compression. The present inventors, after further investigation on this point, found that the above-mentioned fluidized granulation with the use as a raw material of sodium L-ascorbate powder of a particular particle size, even when an amount of a binder used is reduced, can produce granules having satisfactory mechanical strength.

On the basis of these findings, the present inventors conducted a further research study, which culminated in the present invention.

The present invention deals with (1) granules consisting substantially of sodium L-ascorbate and a binder, wherein the content of sodium L-ascorbate is about 98.5 to 99.6 weight %, on dry basis, of the granule, (2) a process for producing sodium L-ascorbate granules, characterized in that said process comprises spraying sodium L-ascorbate powder exhibiting a particle size of not more than 250μ and having its portion of not less than 80 weight % falling into a particle size of not more than 149μ (the JIS standard), while allowing it to fluidize in a fluidized-bed granulator, with a solution containing a binder of such an amount as may correspond to about 0.5 to 1.5 weight % of the total weight of finished product (on dry basis), and granulating while keeping the water content of the composition during the granulating process from not exceeding about 7 weight % throughout the whole process steps, (3) tablets containing sodium L-ascorbate obtained by compressing into tablets the granules consisting substantially of sodium L-ascorbate and a binder, having sodium L-ascorbate comprising about 98.5 to 99.6 weight % on dry basis of the granule and having their portion of not less than about 80 weight % falling into a particle size of 177 to 840μ (the JIS standard) and (4) a method for producing tablets containing sodium L-ascorbate by compressing the granules consisting substantially of sodium L-ascorbate and a binder, having sodium L-ascorbate contained within the range of about 98.5 to 99.5 weight % on dry basis and having their portion of not less than about 80 weight % falling into particle size of 177 to 840μ (the JIS standard).

Sodium L-ascorbate powder, a raw material, which is employed in the preparation of the granules according to the present invention, includes that one exhibiting a particle size of not more than 250μ and having its portion of not less than 80 weight % falling into a particle size of not more than 149μ. Further finely powdered sodium L-ascorbate produces better results. Utilization as a raw material of the powder of the above-mentioned particle size permits the production of the granules having a binder content as low as about 1 weight % or so and being usable as a raw material for the preparation of tablets with satisfactory mechanical strength.

The fluidized-bed granulator comprises fluidized-bed drying equipment fitted with a spraying device and is designed to perform granulating and drying in the same equipment. By way of example, Glatt (made by Glatt AG, West Germany), Aeromatic (made by Aeromatic AG, Switzerland), Calmic (made by Calmic Engineering Co., England), Growmax (made by Fuji Powdal Co., Japan) and Flowcoater (made by Freund Industrial Co., Japan) are mentioned.

Granulating in the fluidized-bed granulator enables the content of water in the composition to be controlled throughout the whole process steps.

The binder, which is useful in the production of the granules, is preferably a water-soluble binder, being exemplified by pregelatinized starch, water-soluble celluloses, water-soluble high-molecular compounds, etc.

The term "pregelatinized starch" designates a kind of starch obtained by dispersing starch in water and heating or one processed further by drying the same. As examples of the pregelatinized starch there may be mentioned pregelatinized corn starch, pregelatinized modified starch (e.g., those as described under Code of Federal Regulation (U.S.A.), §.121. 1031 a, b, c, d, e, f, g or h, etc.) and the like, and the pregelatinized and dried starch, as being made commercially available under the tradenames, e.g. Amicol C (made by Nichiden Chemical Co., Japan), Pre-Gel (made by Hublinger Co., U.S.A.) and Instant Cleargel (made by National Starch Co., U.S.A.), may be utilized.

As examples of the water-soluble celluloses there may be mentioned hydroxypropylcellulose, methylcellulose, hydroxypropyl methylcellulose, etc., while examples of the water-soluble high-molecular compounds include polyvinyl alcohol, gelatin, etc.

Utilization of the above-mentioned binder can afford granules which are usable in the preparation of tablets having satisfactory mechanical strength.

As the solvent which is useful in the preparation of a solution containing the binder, use is made of water. In cases where a binder which is soluble in a mixed solvent of water and alcohols (e.g. ethanol) is used, said mixed solvent may be utilized. In the case of said mixed solvent, concentration of alcohols, practically, is suitably in the range of about 30 to 40 weight %.

Concentration of the binder in the solution containing the same is not specifically limited but, practically, is about 1 to 20 weight/volume % and preferably is in the range of about 5 to 10 weight/volume %.

As the water content of the composition during granulating in the fluidized-bed granulator, the quantity not in excess of about 7 weight % is operable throughout the whole process steps, and it is more preferably recommended that the water content is controlled to the maximal level of about 4 to 6 weight %. By controlling the water content, there can be obtained granules whose color change is depressed.

Changes of the color of the resultant granules can be calculated from readings of a Hunter's tristimulus reflectometer, whereby the unit of the color difference is expressed by NBS (National Bureau of Standard, U.S.A.). In the color difference expressed by NBS, it is known by experience that in cases where a test specimen to be measured is white, if its color difference ($\Delta E$) is not more than 3, no change of color can be discriminated by the naked eye.

As may be obvious from Experiment Example 1 and Examples 1 to 6 as described hereinafter, color change of the granules as produced are all of not more than 3 in color difference ($\Delta E$), and it can therefore be said that the color change of the granules obtained in accordance with the present invention is practically negligible.

In this manner, there can be obtained the sodium L-ascorbate granules consisting substantially of sodium L-ascorbate, having sodium L-ascorbate comprising about 98.5 to 99.5 weight % on dry basis of the granule and having its portion of not less than about 80 weight % falling into a particle size of 177 to 840μ.

More particularly, there can be produced the sodium L-ascorbate granules having the particle size distribution: not more than about 15 weight % falling less than 177μ, not less than about 80 weight % between 177 and 840μ and not more than about 5 weight % in excess of 840μ.

Thus, the process according to the present invention can produce granules having an exceedingly low content of the binder and a high content of sodium L-ascorbate.

And, the angle of repose of such granules is 38° in average.

In short, by subjecting sodium L-ascorbate powder of a particular particle size to fluidized-bed granulation while controlling its water content, there can be prepared granules with a depressed degree of color change and with such a satisfactory mechanical strength as explained later, by the use of a remarkably small amount of a binder for coating.

The sodium L-ascorbate granules obtained by the process of the present invention offer the following advantageous features. That is to say, because of an exceedingly small amount of the binder required, nearly the whole portion consists of sodium L-ascorbate, and requirement of a small amount of the binder justifies the use of a decreased quantity of water and also facilitates the control of water content during granulation, thereby resulting in an extremely depressed degree of color change; and said granules, with their excellent flowability provide the good weight uniformity to the resultant tablets in the case of compression into tablets, and the enhanced easiness of tablet processing by compression can make operation of the tablet machine faster; furthermore, the appearance of said granules is good.

The sodium L-ascorbate granules according to the present invention can be utilized as the raw material in the manufacture of tablets containing sodium L-ascorbate.

Compression of said granules into tablets is conducted, in accordance with the conventional processes, in the presence of a lubricant as well as further L-ascorbic acid granules or excipients (e.g., lactose, sucrose, mannitol, etc.), as the case may be. As the lubricant, there may be mentioned those employed normally in the manufacture of tablets such as stearates (e.g., magnesium stearate, calcium stearate, and stearic acid) and talc. The amount and kind of said lubricant are selected in such a range of variation as may yield tablets being practical in terms of mechanical strength and disintegration. Normally, its amount is suitably used in the proportion of about 0.1 to about 7 weight % against the principal pharmaceutical component, and stearates, among others, are desirably added in the proportion of at least about 0.5% against the pharmaceutical component.

Mixing the granules of the present invention with the lubricant, followed by compression into tablets, permits the production of tablets having satisfactory mechanical strength, while maintaining the content of sodium L-ascorbate at a high level. Utilization of the above-mentioned amount of the lubricant for processing into tablets can yield the tablets containing about 94 to 98 weight % of sodium L-ascorbate. In addition, the method of the present invention can provide tablets containing the sodium L-ascorbate amount per tablet of about 100 to about 2000 mg and, preferably from a practical point of view, about 400 to 600 mg. The method of the present invention can afford tablets having tensile strength of not less than 12.5 kg/cm² sufficiently to be put into practical use. Normally, it is usual that the tablets with high mechanical strength retards the disintegration time. In contrast to this, the disintegration time of the tablets obtained by the method of the present invention falls within the standard of the Japanese Pharmacopeia, and said method is satisfactory in terms of this point.

Furthermore, the granules, when they are processed into tablets, can yield tablets with by far lessened change of color.

The relationship between hardness and tensile strength of a tablet is expressed by the following equation:

$$\delta = \frac{2P}{\pi DT} \text{ (kg/cm}^2\text{)}$$

wherein δ designates tensile strength, P hardness, D diameter of a tablet, and T thickness of a tablet, respectively. As far as tablets are concerned, the tablets having tensile strength of not lower than $\delta = 12.5$ kg/cm² can be put into practical use.

As examples of the L-ascorbic acid granules in the presence of which compression into tablets is carried out, there may be mentioned the L-ascorbic acid granules obtained by the method which comprises spray-coating L-ascorbic acid powder passing through a 200-mesh (Tyler standard), while allowing it to fluidize in a fluidized-bed granulator, with a solution containing about 1 to about 10 weight % of the binder to thereby contain the binder of about 2 to about 4 weight % against L-ascorbic acid.

In the case of compression being conducted in the presence of L-ascorbic acid granules, a ratio of sodium L-ascorbate granules against L-ascorbic acid granules is in the range of about 40 to 60:60 to 40, and preferably in the range of about 45 to 55:55 to 45.

Even when the granules according to the present invention are compressed into tablets in the presence of L-ascorbic acid granules, tablets having satisfactory mechanical strength can be produced. In addition, such tablets possess the advantageous properties, like the above-mentioned sodium L-ascorbate tablets, in terms of an increased content of sodium L-ascorbate and L-ascorbic acid, uniform tablet weight, prompt tablet disintegration time and depressed color change.

Furthermore, the tablets consisting solely of L-ascorbic acid have an acid taste and are in some instances disliked by some persons, whereas the tablets consisting of a combination of it with sodium L-ascorbate can reduce such acid taste.

The particle size as used herein is based on the JIS (Japanese Industrial Standard), unless otherwise specified. The relationship in particle size among the JIS, ASTM (American Standard for Testing Materials) standard and W. S. Tyler standard is as shown below, and the particle size as specified in the JIS is construed to designate the corresponding particle sizes of the ASTM and Tyler standard.

| JIS | | ASTM | | Tyler | |
|---|---|---|---|---|---|
| Nominal size, $\mu$ | Sieve opening, $\mu$ | Nominal number | Sieve opening, $\mu$ | Nominal No., mesh | Sieve opening, $\mu$ |
| 149 | 149 | 100 | 149 | 100 | 147 |
| 177 | 177 | 80 | 177 | 80 | 175 |
| 250 | 250 | 60 | 250 | 60 | 246 |
| 840 | 840 | 20 | 840 | 20 | 833 |
| 1000 | 1000 | 18 | 1000 | 16 | 991 |

Given below are the Experiment Examples, Reference Example and Examples to illustrate more specifically the present invention; "part(s)" represents "part(s) by weight", unless otherwise specified, while "%" designates "weight %", unless otherwise specified; the particle size is in accordance with the JIS, unless otherwise specified.

EXPERIMENT EXAMPLE 1

(1) Experimental method (I) Method for producing granules

While using as the raw material sodium L-ascorbate powder of not more than 149$\mu$ in particle size, together with use of a starch paste (pregelatinized starch), granulation was carried out by the following processes, and colors of the resultant granules were measured for comparison.

(a) Method for producing granules by a fluidized granulation process

In the fluidized-bed granulator (Glatt-Okawara, WSG-5) was charged 10 kg of sodium L-ascorbate powder, which was allowed to fluidize by air heated at 80° C. A pregelatinized starch solution prepared by heating a 5% (W/V) dispersion of corn starch at 90° C. was cooled down to 50° C. and, while keeping a sprayed amount of the solution under control not to allow the water content of the composition to exceed 5 weight % during granulation, the granulation was carried out. The spraying was suspended at the time when the pregelatinized starch of 1 weight % on dry basis was sprayed, followed by drying to manufacture the granules.

(b) Method for producing granules by a kneading process

In a Pony Mixer (manufactured by Inoue Seisakusho, Japan) with a capacity of 15 U.S. gallons was charged 10 kg of sodium L-ascorbate powder. A pregelatinized starch solution prepared separately by heating a 10% (W/V) dispersion of corn starch was cooled to 50° C., and charged in once into the mixer to initiate kneading. After kneading for 20 minutes, the mixture was dried under vacuum at 40° C. for 16 hours. The mass was granulated by passing through a Fitz-Patrick mill (manufactured by Hosokawa Iron Works Inc., Japan). In this case, the amount of the binder used was at 1% (W/W).

(II) Colorimetry

About 1 g each of the raw material powder, the granules as produced by a fluidized granulation process under the above-mentioned (I) (a) and the granules as produced by a kneading process under (I) (b) were compressed with use of a die of 20 mm diameter and punches at a pressure of about 1 ton/cm$^2$, respectively, to produce small discs. The color of discs was measured with SM Color Computer (made by Suga Testing Equipment Co., Japan), tristimulus reflectometer.

(2) Results of Experiment

Results of the measurements, as expressed in $\Delta E$ (color difference) with color of the raw material taken as a standard, are as follows, whereby a change of color may be clearly discernible to the naked eye, when $\Delta E$ is not less than 3 (NBS unit) in the case of a white specimen.

| Discs | $\Delta E$ (NBS unit) |
|---|---|
| Discs from the granules under (a) | 1.16 |
| Discs from the granules under (b) | 8.22 |

As is apparent from the above, the granules produced by the kneading process are observed to be distinctly colored, whereas there is hardly observed any coloration with the granules produced by the method according to the present invention.

EXPERIMENT EXAMPLE 2

The particle size was measured with the sodium L-ascorbate granules produced by the fluidized granulation process and the kneading process in Experiment Example 1 respectively. Results obtained are shown below.

| | Granules | |
|---|---|---|
| Size of particles | Granules produced by the method of the present invention | Granules produced by the kneading process |
| Portion remaining on the 840$\mu$ sieve. | 1.4 weight % | 14.0 weight % |
| Portion passing through the 840$\mu$ sieve but remaining on the 500$\mu$ sieve. | 29.9 weight % | 23.5 weight % |
| Portion passing through the 500$\mu$ sieve but remaining | | |

| Size of particles | Granules | |
|---|---|---|
| | Granules produced by the method of the present invention | Granules produced by the kneading process |
| on the 177μ sieve. | 65.2 weight % | 39.0 weight % |
| Portion passing through the 177μ sieve. | 3.5 weight % | 23.5 weight % |

As is obvious from the above, there is the distinct difference in particle size between the granules produced by the method of the present invention and by the kneading process.

Comparative study on the flowability of the granules by means of the method of Gold et. al. [Journal of Pharmaceutical Science, 57, 2153 (1968)] indicates that the granules produced by the method of the present invention flow out of a funnel with a 10-mm diameter at a highly uniform rate of about 19 g per second, whereas those by the kneading process flow out at an extremely irregular rate averaging about 14 g per second but varying from about 0 g per second to about 26 g per second.

REFERENCE EXAMPLE 1

A 97 parts portion of ground powdery L-ascorbic acid, which passed through a 200-mesh (Tyler standard) sieve, 4.5% of which remained on a 250-mesh (Tyler standard) sieve and 82.8% of which passed through a 325-mesh (Tyler standard) sieve, was flown in a fluidized-bed granulator. To the powder was sprayed a paste solution prepared by pregelatinizing a 5.0 weight % aqueous suspension of corn starch at 85° C. and cooling to 50° C. The spraying was stopped at the time when the starch paste solution of 3 parts as converted to the starch weight was sprayed, and drying in situ was conducted. The granules obtained in this manner were pulverized through a Fitz-mill (manufactured by Hosokawa Iron Works Inc., Japan) with use of a 1.0 mm screen to obtain L-ascorbic acid granules.

EXAMPLE 1

A 99.5 parts portion of sodium L-ascorbate not larger than 149μ in particle size was fluidized in a fluidized-bed granulator. A starch paste prepared by pregelatinizing a 5 weight % aqueous dispersion of corn starch at 85° C. was cooled to 50° C., and sprayed in the amount corresponding to 0.5 part on a solid basis to the sodium L-ascorbate powder, while keeping the water content of the composition during the granulation from exceeding the maximum 6 weight %, to thus conduct granulation. The particle size of the resultant granules is shown below.

| Less than 177μ | 177 to 840μ | over 840μ |
|---|---|---|
| 13.5 weight % | 84.5 weight % | 2.0 weight % |

With the granules thus obtained, the extent of change of color against the raw material of sodium L-ascorbate was determined by means of the measuring method as described in Experiment Example 1, thereby resulting in ΔE=0.96 (NBS unit).

To 95.5 parts of the granules obtained as above, there were added for mixing 4.0 parts of spray-dry lactose and 0.5 part of magnesium stearate, and the mixture was compressed into 527-mg tablets with beveled edge flat face, thereby yielding tablets with 500 mg of a content of sodium L-ascorbate. The tablets obtained exhibited tensile strength of 22.3 kg/cm$^2$.

EXAMPLE 2

A 99 parts portion of sodium L-ascorbate not larger than 149μ in particle size was fluidized in a fluidized-bed granulator. A starch paste solution obtained by pregelatinizing a 5 weight % dispersion of corn starch in water at 90° C. was sprayed in an amount corresponding to 1 part on a solid basis onto the powder, while controlling a water content of the composition during the granulation in such a way that it might not exceed the maximum 5.5 weight %, to thus conduct granulation. The particle size of the resultant granules is shown below.

| Less than 177μ | 177 to 840μ | Over 840μ |
|---|---|---|
| 10.0 weight % | 87.0 weight % | 3.0 weight % |

With the granules thus obtained, the extent of change of color against the raw material of sodium L-ascorbate was determined by means of the measuring method as described in Experiment Example 1, thereby resulting in ΔE=1.01 (NBS unit).

Admixed with 99.5 parts of the granules obtained as above was 0.5 part of magnesium stearate, and the mixture was compressed into 508 mg tablets with beveled edge flat face, thereby yielding tablets with 500 mg of a content of sodium L-ascorbate. The obtained tablets exhibited tensile strength of 19.8 kg/cm$^2$.

EXAMPLE 3

A 98.5 parts portion of sodium L-ascorbate not larger than 177μ in particle size was fluidized in a fluidized-bed granulator. An adequately uniform paste solution obtained by pregelatinizing a 5 weight % dispersion of Amicol C in water was sprayed in an amount corresponding to 1.5 parts on a solid basis onto the powder, while keeping the water content of the composition during the granulation from exceeding the maximum 5.0 weight %, to thus conduct granulation. The particle size of the resultant granules is shown below.

| Less than 177μ | 177 to 840μ | Over 840μ |
|---|---|---|
| 9.5 weight % | 87.0 weight % | 3.5 weight % |

With the granules thus obtained, the extent of change of color against the raw material of sodium L-ascorbate was determined by means of the measuring method as described in Experiment Example 1, thereby resulting in ΔE=0.95 (NBS unit).

Admixed with 99.5 parts of the granules obtained as above was 0.5 part of magnesium stearate, and the mixture was compressed into 511-mg tablets with beveled edge flat face. 500 mg of sodium L-ascorbate was found to be contained in one of these tablets. The obtained tablets exhibited tensile strength of 21.5 kg/cm$^2$.

EXAMPLE 4

A 99 parts portion of sodium L-ascorbate not larger than 250μ in particle size, 90 weight % of which fell in the range of not larger than 149μ, was fluidized in a fluidized-bed granulator, whereby a 5 weight % aqueous solution of hydroxypropylcellulose was sprayed in an amount corresponding to 1 part on a solid basis onto the powder, while controlling a water content of the mixture during the granulating in such a way that it might not exceed the maximum 5.0 weight %, to thus conduct granulation. The particles size of the resultant granules is shown below.

| Less than 177μ | 177 to 840μ | Over 840μ |
| --- | --- | --- |
| 11.5 weight % | 86.5 weight % | 2.0 weight % |

With the granules thus obtained, the extent of change of color against the raw material of sodium L-ascorbate was determined by means of the measuring method as described in Experiment Example 1, thereby resulting in $\Delta E = 1.05$ (NBS unit).

Admixed with 99.5 parts of the granules obtained as above was 0.5 part of magnesium stearate, and the mixture was compressed into 508-mg tablets with beveled edge flat face, thereby yielding the tablets with 500 mg of a content of sodium L-ascorbate. The obtained tablets exhibited tensile strength of 17.7 kg/cm$^2$.

EXAMPLE 5

Granulation was conducted under the same conditions as described in Example 4, except that a 5 weight % hydroxypropylcellulose solution prepared with use as a solvent of an aqueous solution containing 30 weight % of ethanol was employed in place of the 5 weight % aqueous solution of hydroxypropylcellulose. The particle size of the resultant granules is shown below.

| Less than 177μ | 177 to 840μ | Over 840μ |
| --- | --- | --- |
| 10.5 weight % | 87.5 weight % | 2.0 weight % |

With the granules thus obtained, the extent of change in color against the raw material of sodium L-ascorbate was determined by means of the measuring method as described in Experiment Example 1, thereby resulting in $\Delta E = 0.85$ (NBS unit). 0.5 part of magnesium stearate was admixed with 99.5 parts of the granules obtained as above, and the mixture was compressed into 508 mg tablets with beveled edge flat face, thereby yielding tablets with 500 mg of a content of sodium L-ascorbate. The obtained tablets exhibited tensile strength of 18.5 kg/cm$^2$.

EXAMPLE 6

A 99 parts portion of sodium L-ascorbate not larger than 250μ in particle size, 90 weight % of which fell in the range of not larger than 149μ, was fluidized in a fluidized-bed granulator, whereby a 5 weight % aqueous solution of polyvinyl alcohol was sprayed in the amount corresponding to 1 part on a solid basis onto the powder, while controlling the water content of the mixture during the granulation not to exceed the maximum 5.0 weight %, to thus conduct granulation. The particle size of the resultant granules is shown below.

| Less than 177μ | 177 to 840μ | Over 840μ |
| --- | --- | --- |
| 7.5 weight % | 88.5 weight % | 4.0 weight % |

With the granules thus obtained, the extent of change in color against the raw material of sodium L-ascorbate was determined by means of the measuring method as described in Experiment Example 1, thereby resulting in $\Delta E = 0.86$ (NBS unit).

0.5 part of magnesium stearate was admixed with 99.5 parts of the granules obtained as above, and the mixture was compressed into 508-mg tablets with beveled edge flat face, thereby yielding tablets with 500 mg of a content of sodium L-ascorbate. The obtained tablets exhibited tensile strength of 18.3 kg/cm$^2$.

EXAMPLE 7

A 0.5 part portion of magnesium stearate was admixed with 47.4 parts of L-ascorbic acid granules (L-ascorbic acid content: 97%) as obtained in Reference Example 1 and 52.1 parts of sodium L-ascorbate granules (Sodium L-ascorbate content: 99%) as obtained in Example 2, and the mixture was compressed into 513-mg tablets with beveled edge flat face, thereby yielding tablets each containing 500 mg of the substance as converted into L-ascorbic acid. The obtained tablets exhibited tensile strength of 20.6 kg/cm$^2$.

What we claim is:

1. Sodium L-ascorbate granules consisting substantially of sodium L-ascorbate and a binder, wherein the content of sodium L-ascorbate is from about 98.5 to 99.5 weight percent, on dry basis, of the granule and not less than about 80 weight percent of the granule having a particle size of 177 to 840μ which are produced by spraying sodium L-ascorbate powder having a particle size of not more than 250μ and not less than about 80 weight percent of said powder having a particle size of not more than 149μ, while allowing it to fluidize in a fluidized-bed granulator, with a solution containing a binder in an amount corresponding to about 0.5 to 1.5 weight percent of the total weight of finished product on a dry basis, and while maintaining the water content of the composition during the granulating process below about 7 weight percent throughout the entire process.

2. Granules as claimed in claim 1, wherein the binder is a pregelatinized starch, a water-soluble cellulose or a water-soluble high-molecular compound.

3. Granules as claimed in claim 2, wherein the pregelatinized starch is pregelatinized cornstarch.

4. Granules as claimed in claim 2, wherein the water-soluble cellulose is hydroxypropylcellulose.

5. Granules as claimed in claim 2, wherein the water-soluble high-molecular compound is polyvinyl alcohol.

6. A method for producing sodium L-ascorbate granules, which comprises spraying sodium L-ascorbate powder having a particle size of not more than 250μ and not less than about 80 weight percent of said powder having a particle size of not more than 149μ, while allowing it to fluidize in a fluidized-bed granulator, with a solution containing a binder in an amount corresponding to about 0.5 to 1.5 weight percent of the total weight of finished product on a dry basis, and granulating the mixture while maintaining the water content of the composition during the granulating process below about 7 weight percent throughout the entire process.

7. A method according to claim 6, wherein the binder is a pregelatinized starch, a water-soluble cellulose or a water-soluble high-molecular compound.

8. A method according to claim 7, wherein the pregelatinized starch is pregelatinized cornstarch.

9. A method according to claim 7, wherein the water-soluble cellulose is hydroxypropylcellulose.

10. A method according to claim 7, wherein the water-soluble high-molecular compound is polyvinyl alcohol.

11. Tablets containing sodium L-ascorbate obtained by compressing into tablets granules consisting substantially of sodium L-ascorbate and a binder, the granules comprising sodium L-ascorbate within the range of about 98.5 to 99.5 weight percent on a dry basis of the granule and not less than about 80 weight percent of the granule having a particle size of 177 to 840μ and being produced by spraying sodium L-ascorbate powder having a particle size of not more than 250μ and not less than about 80 weight percent of said powder having a particle size of not more than 149μ, while allowing it to fluidize in a fluidized-bed granulator, with a solution containing a binder in an amount corresponding to about 0.5 to 1.5 weight percent of the total weight of finished product on a dry basis, and while maintaining the water content of the composition during the granulating process below about 7 weight percent throughout the entire process.

12. Tablets containing sodium L-ascorbate as claimed in claim 11, wherein said tablets are obtained by compression in the presence of L-ascorbic acid granules.

13. A tablet according to claim 11, wherein the binder is a pregelatinized starch, a water-soluble cellulose, or a water-soluble high-molecular compound.

14. A tablet according to claim 13, wherein the pregelatinized starch is pregelatinized cornstarch.

15. A tablet according to claim 13, wherein the water-soluble cellulose is hydroxypropylcellulose.

16. A tablet according to claim 13, wherein the water-soluble high-molecular compound is polyvinyl alcohol.

17. A method for producing tablets containing sodium L-ascorbate by compressing granules consisting substantially of sodium L-ascorbate and a binder, the granules comprising sodium L-ascorbate within the range of about 98.5 to 99.5 weight percent on a dry basis and not less than about 80 weight percent of the granule having a particle size of 177 to 840∞ and being produced by spraying sodium L-ascorbate powder having a particle size of not more than 250μ and not less than about 80 weight percent of said powder having a particle size of not more than 149μ, while allowing it to fluidize in a fluidized-bed granulator, with a solution containing a binder in an amount corresponds to about 0.5 to 1.5 weight percent of the total weight of finished product on a dry basis, and while maintaining the water content of the composition during the granulating process below about 7 weight percent throughout the entire process.

18. A method as claimed in claim 17, wherein the compression is conducted in the presence of L-ascorbic acid granules.

19. A method according to claim 17, wherein the binder is a pregelatinized starch, a water-soluble cellulose or a water-soluble high-molecular compound.

20. A method according to claim 19, wherein the pregelatinized starch is pregelatinized cornstarch.

21. A method according to claim 19, wherein the water-soluble cellulose is hydroxypropylcellulose.

22. A method according to claim 19, wherein the water-soluble high-molecular compound is polyvinyl alcohol.

* * * * *